United States Patent [19]
Hu et al.

[11] Patent Number: 5,763,110
[45] Date of Patent: Jun. 9, 1998

[54] ELECTROLUMINESCENT DEVICES COMPRISING POLYNUCLEAR ARYLAMINES

[75] Inventors: Nan-Xing Hu, Oakville; Beng S. Ong, Mississauga; Shuang Xie, Mississauga; Zoran D. Popovic, Mississauga; Ah-Mee Hor, Mississauga, all of Canada

[73] Assignee: Xerox Corporation, Stamford, Conn.

[21] Appl. No.: 707,162

[22] Filed: Sep. 3, 1996

[51] Int. Cl.$^6$ ............................... H05B 33/00
[52] U.S. Cl. .............. 428/690; 428/704; 428/917; 428/457; 428/215; 313/504; 313/506
[58] Field of Search .................... 428/690, 917, 428/457, 704, 215; 313/504, 506

[56] References Cited

U.S. PATENT DOCUMENTS

| | | |
|---|---|---|
| 4,356,429 | 10/1982 | Tang ............................ 313/503 |
| 4,539,507 | 9/1985 | Van Slyke et al. ............ 313/504 |
| 4,769,292 | 9/1988 | Tang et al. .................... 428/690 |
| 4,950,950 | 8/1990 | Perry et al. ................... 313/504 |

FOREIGN PATENT DOCUMENTS

| | | |
|---|---|---|
| 0 650 955 A1 | 5/1995 | European Pat. Off. . |
| 8-179526 | 7/1996 | Japan . |

*Primary Examiner*—Marie Yamnitzky
*Attorney, Agent, or Firm*—E. O. Palallo

[57] ABSTRACT

An electroluminescent device comprised of a polynuclear arylamine as represented by the formula (I) wherein $R^1$, $R^2$, $R^3$, $R^4$, $R^5$ and $R^6$ are aryl groups, $A^1$ and $A^2$ are biaryl groups, and P is a hydrocarbon bridge.

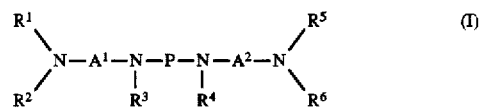

14 Claims, 1 Drawing Sheet

ELECTROLUMINESCENT DEVICES COMPRISING POLYNUCLEAR ARYLAMINES

REFERENCE TO PENDING APPLICATIONS

Illustrated in copending patent application, U.S. Ser. No. 08/404,260, the disclosure of which is totally incorporated herein by reference, is an electroluminescent device comprised of polynuclear arylamines of the formula (I)

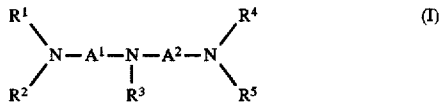

wherein $R^1$, $R^2$, $R^3$, $R^4$, and $R^5$ are aryl groups, and $A^1$ and $A^2$ are biaryl groups; and U.S. Pat. No. 5,674,635, the disclosure of which is totally incorporated herein by reference, is an EL device comprising a polymer of a tetraaryl-substituted biphenyldiamine, such as a copolymer of N,N'-diphenyl-N,N'-bis(3-hydroxyphenyl)-1,1'-biphenyl-4,4'-diamine with a member selected from the group consisting of bisphenyl-A-bischloroformate, ethyleneglycol bischloroformate, diethyleneglycol bischloroformate, adipolychloride, suberoylchloride and sebacoylchloride, or a siloxane based N,N'-diphenyl-N,N'-bis(3-hydroxyphenyl)-1,1'-biphenyl-4,4'-diamine polymer.

BACKGROUND OF THE INVENTION

This invention is generally directed to electroluminescent (EL) devices, and more specifically, to organic EL devices with enhanced thermal and operational stability, and thus improved durability, and which devices contain certain large, lability-limited polynuclear arylamines as hole transport components, which devices can be selected as flat panel displays and image bar components for digital copiers and printers.

Electrooptical devices, such as cathode ray tubes (CRTs), are known. However, these devices are very bulky in size and consume substantial amounts of energy. Furthermore, it is difficult to manufacture a cost-effective distortion-free or low-distortion display based on known CRT technology. Accordingly, there has been a continuing interest in developing a compact flat-panel display device which optimizes space usage, and operates at low voltages of, for example, below 20 volts. Illustrative examples of these include liquid crystal displays and others that are compatible with integrated circuit drivers, such as an array of thin film transistors illustrated by T. S. Perry and P. Wallick, *IEEE Spectrum* 22 No. 7, 52 (1985); L. E. Tannas, Jr., *IEEE Spectrum* 23 No. 10, 37 (1986); and L. E. Tannas, Jr., *IEEE Spectrum* 26 No. 9, 34 (1989), the disclosures of which are totally incorporated herein by reference.

From the energy and space usage, and display viewing angle flexibility perspectives, particular attention has been devoted to developing energy-efficient flat-panel displays which are capable of providing a clear display without restricted viewing angles. Currently, the majority of the flat-panel display devices are based on the liquid crystal display concept, which technology is, however, beset with the problems of slow response time and restricted viewing angle limitations. The electroluminescence-type display concept appears to offer an ideal solution to resolving some if not all these difficulties. However, many EL devices are based on inorganic materials, and generally require high driving voltages. Organic EL devices may offer the advantage of lower driving voltages, but their current performance shortfalls, such as short serviceable life and low EL efficiency, have presented challenging technological hurdles to their practical applications. One of the objectives of the present invention is, therefore, to provide organic EL devices with a prolonged serviceable life span, and a high level of EL efficiency characteristics.

A simple organic EL device is comprised of a layer of organic luminescent material conductively sandwiched in between an anode typically comprised of a transparent conductor, such as indium-tin oxide and a cathode, typically a low work-function metal, such as magnesium, or calcium, aluminum, or its alloy with other metals. The device functions on the principle that under an electric field, positive charges (holes) and negative charges (electrons) are respectively injected from the anode and cathode into the luminescent layer and undergo recombination to form excitonic states which subsequently emit light. Prior art organic EL devices have been constructed from a laminate of an organic luminescent material and electrodes of opposite polarity, which devices include a single crystal material, such as single crystal anthracence, as the luminescent substance as described, for example, in U.S. Pat. No. 3,530,325. However, these devices required excitation voltages on the order of 100 volts or greater. Subsequent modifications of the device structure through incorporation of additional layers, such as charge injecting and charge transport layers, have led to significant performance improvement. More recently, organic EL devices comprised of multi-layered thin films of organic materials provide several advantages including low operating voltages of less than 20 volts and high luminance of greater than a few hundred $cd/m^2$. Illustrative examples of this type of EL devices have been disclosed in publications by Tang et al. in *J. Appl. Phys.* vol. 65, pp. 3610 to 3616 (1989) and Saito et al. in *Mol. Cryst. Liq. Cryst.* vol. 253, pp. 125 to 132 (1994), the disclosures of which are totally incorporated herein by reference. Further known is the fabrication of organic EL devices such as those based on poly(p-phenylene vinylene), J. H. Burroughes et al., *Nature* 347, 539 (1990).

Moreover, U.S. Pat. No. 4,950,950 illustrates a multilayer EL device with silane hole transporting agents. U.S. Pat. No. 4,356,429 illustrates organic EL cells with a hole injecting porphyrinic zone. P. S. Vincett, W. A. Barlow, R. A. Hann and G. G. Roberts, *Thin Solid Films* 94, 171 (1982); R. H. Partridge, *Polymer* 24, 755 (1983); J. H. Burroughes et al., *Nature*, supra; D. Braun and A. J. Heeger, *Applied Physics Letters* 58, 1982 (1991); D. Braun and A. J. Heeger, *J. Electronic Materials* 20, 945 (1991); A. R. Brown et al., *Applied Physics Letters* 61, 2793 (1992), and J. Kido et al., *Applied Physics Letters* 59,2760 (1991) disclose EL compositions.

In one configuration, the EL device organic layer is comprised of a host organic polymer layer that supports hole injection from the anode and electron injection from the cathode, and is capable of emitting light in response to subsequent electron-hole recombination. This host organic polymer layer can further include a compound that facilitates hole injection, a compound that facilitates electron injection and, optionally, a fluorescent material capable of emitting light in response to recombination of holes and electrons.

An EL device with organic dual layer structure comprises one layer adjacent to the anode supporting hole injection and transport, and another layer adjacent to the cathode supporting electron injection and transport. The recombination of charge carriers and subsequent emission of light occurs in one of the layers near the interface between the two layers.

Optionally, a fluorescent material can be added to one of the layers leading to the recombination of charge carriers and emission of light occurring in that compound.

In another configuration, an EL device comprises three separate layers, a hole transport layer, an emission layer, and an electron transport layer, which are laminated in sequence and are sandwiched as a whole between an anode and a cathode.

A method of fabricating organic EL devices with layered structures is by vacuum vapor deposition as illustrated in U.S. Pat. No. 4,769,292. Accordingly, EL materials for the charge transport and the organic luminescent layers are those that can be readily vacuum deposited as thin films. Of particular importance to the fabrication of EL devices is the proper selection of organic materials, especially the hole injecting and transporting materials which can affect the device performance. In U.S. Pat. No. 4,356,429 is described EL devices containing a porphyrinic compound as hole injecting layer between the luminescent zone and the anode, while in U.S. Pat. No. 4,539,507, the use of amines as hole injecting layer to improve the light output efficiency of organic EL devices is disclosed. Specific amines claimed in the '507 patent include bis(4-dimethylamino-2-methylphenyl)phenylmethane, N,N,N,-tri(p-tolyl)amine, 1,1,-bis(4-di-p-tolylaminophenyl)cyclohexane, and 1,1,-bis(4-di-p-tolylaminophenyl)-4-phenylcyclohexane. In addition, the use of tetraphenyldiamine as hole transport material in three-layer organic EL devices was described by C. Adachi et al. in *Jpn. J. Appl. Phys.*, Vol. 27, L269 to L271, 1988. The disclosures of each of the above mentioned patents and publications are totally incorporated herein by reference.

While certain hole transporting materials are generally known to facilitate hole injection and hole transport processes which lead to improved device performance for organic EL devices, there are some critical issues associated with these materials, notably the thermal and operational stabilities of these materials as amorphous films. Prior art amine hole injecting and transport layers generally suffer from poor thermal and operational stability arising primarily from the crystallization of the amine molecules in the thin-film hole injecting and transport layers.

A recent approach to resolving the thermal stability issue of amine hole injecting and transport layer is to incorporate the amine transport moiety in a polymer structure. In U.S. Pat. No. 5,674,625, there is illustrated an electroluminescent device comprising a polymer of a tetraaryl-substituted biphenyldiamine, such as a copolymer of N,N'-diphenyl-N,N'-bis(3-hydroxyphenyl)-1,1'-biphenyl-4,4'-diamine with a member selected from the group consisting of bisphenyl-A-bischloroformate, ethyleneglycol bischloroformate, diethyleneglycol bischloroformate, adipoylchloride, suberoylchloride and sebacoylchloride, or a siloxane based N,N'-diphenyl-N,N'-bis(3-hydroxyphenyl)-1,1'-biphenyl-4,4'-diamine polymer. In this application, the hole transport polymers are deposited by solution coating techniques, such as spin coating, dip coating, and spray coating, which obviously impose certain restrictions on the manufacturing processes. These polymeric amines in thin film of submicron thickness can not be prepared by vacuum deposition technique as they tend to decompose during the thermal heating process. Furthermore, the synthesis and purification of polymeric hole transport materials are generally tedious and labor intensive.

In view of the above-mentioned complexities and difficulties when selecting polymeric charge carrier transport components, the invention charge carrier components have been developed, particularly hole transport materials, which can be readily fabricated into thin film charge transport layers by vacuum deposition techniques. Specifically, the invention components are directed to a new class of large polynuclear arylamines, which possess excellent thermal stability and can be readily sublimed or evaporable under high vacuum to form stable thin film hole injecting and transport layers. These arylamines by virtue of their large size and steric bulkiness exhibit an excellent resistance towards crystallization when deposited as thin films. They, therefore, can function as thermally and morphologically stable hole injecting and transporting components for EL devices. Suitable performance-enhancing luminescent additives, such as fluorescent dyes, can be incorporated into the arylamine layer by codeposition to further improve the device luminescence efficiency and durability.

BRIEF DESCRIPTION OF THE FIGURES

Illustrated in FIGS. 1 and 2 are examples of EL devices of the present invention.

SUMMARY OF THE INVENTION

Figure 1:
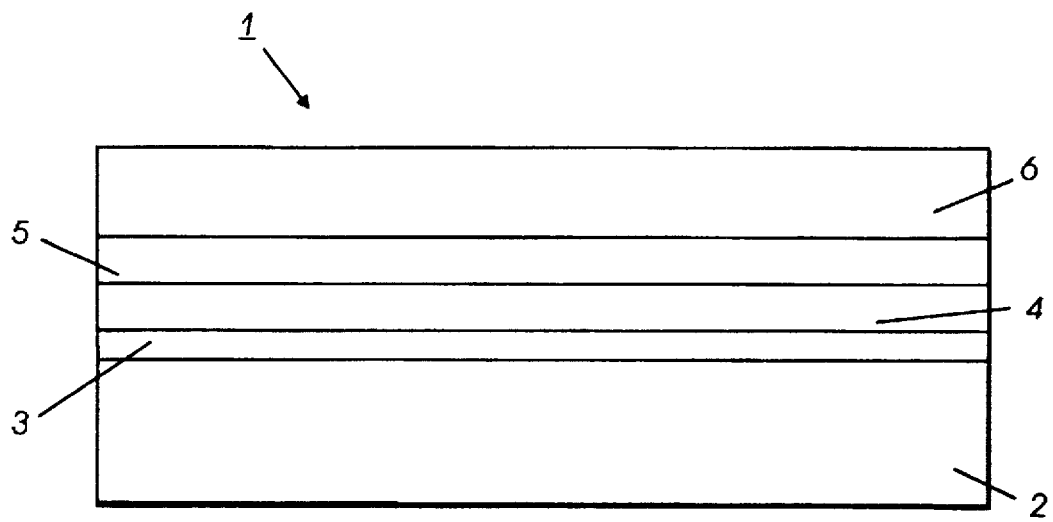

Examples of objects of the present invention include:

It is an object of the present invention to provide EL devices with many of the advantages illustrated herein.

Another object of the present invention is to provide EL devices with enhanced thermal and operational stability.

In another object of the present invention there are provided improved EL devices which exhibit high electroluminescence efficiency at relatively low operating voltages of below 20 volts.

A further object of the present invention is the provision of large, lability-limited polynuclear arylamines as the hole injecting and hole transporting components for EL devices.

In an associated object of the present invention there are provided synthetic processes for the preparation of large, lability-limited hole injecting, and transporting polynucleararylamines.

In a further object of the present invention there are provided EL devices comprised of a supporting substrate of, for example, glass, an anode, a vacuum deposited organic hole transport layer comprised of large, lability-limited polynuclear arylamines, a vacuum deposited electron transport layer, and in contact therewith a low work function metal as a cathode.

In yet another object of the present invention there are provided improved EL devices comprised of a vacuum deposited layer of an electron injecting and transporting component, an optional light emitting material, and a hole injecting and transporting component of large, lability-limited polynuclear arylamine, and which layer is sandwiched in between a cathode and an anode.

A further object of the present invention is the provision of large, lability-limited polynuclear arylamine compounds which possess excellent thermal stability, and can be readily vacuum deposited as thermal and morphologically stable amorphous thin films for use as hole injecting and hole transporting components in EL devices.

These and other objects of the present invention are accomplished in embodiments thereof by the provision of layered organic EL devices which contain certain large, lability-limited polynuclear arylamine hole injecting and transporting molecules as indicated herein, and which devices possess a number of advantages including improved thermal and operational stability, excellent durability, high electroluminescence efficiency, and which devices can be readily fabricated using vacuum deposition techniques. The large, lability-limited polynuclear arylamines of the present invention possess superior thermal stability, and excellent resistance to decomposition or structural changes during vacuum evaporation process, wherein during such processes thermally and morphologically stable hole injecting and transporting thin films of the polyarylamines are formed. The EL devices with these arylamines exhibit improved thermal and operational stability, and excellent device durability at temperatures around and above 40° C. In embodiments, the present invention relates to EL devices that are comprised of an anode, an organic hole injecting and transporting component, an electron transport component, and a cathode, and wherein the hole injecting and transporting component is an evaporated thin film of a large, lability-limited polynuclear arylamine of formula (I). In embodiments the present invention relates to an EL device comprised of a single luminescent layer of a polynuclear arylamine hole injecting and hole transporting component of and encompassed formula (I), and an electron injecting and transporting component, optionally doped with a light emitting fluorescent material, and sandwiched between an anode and a cathode

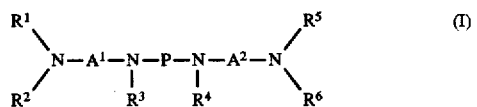

wherein $R^1$, $R^2$, $R^3$, $R^4$, $R^5$, and $R^6$ are aryl groups with, for example, from 6 to about 30 carbon atoms, such as phenyl, tolyl, xylyl, chlorophenyl, naphthyl, and the like; P is a hydrocarbon bridge like an alkylene, or arylene with, for example, from about 1 to about 30 carbon atoms, such as methylene, dimethylmethylene, 1,1-cyclohexylene, ethylene, polymethylene, arylenes such as diphenylmethylene, phenylene, tolylene, xylylene, and chlorophenylene; $A^1$ and $A^2$ are biaryl groups with from about 12 to about 60 carbon atoms, such as biphenyl, bitolyl, and the like, and wherein in embodiments the aforementioned groups may be substituted with, for example, halogen.

DESCRIPTION OF PREFERRED EMBODIMENTS

Figure 2:
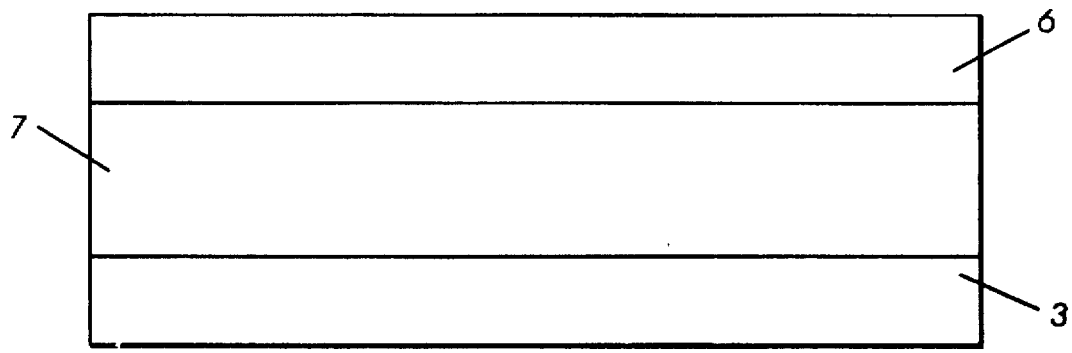

The embodiments of the present invention will be described in more detail with reference to the schematic diagrams of EL devices as depicted in FIGS. 1 and 2

FIG. 1 illustrates an EL device which comprises an organic light emitting diode 1 comprised of a supporting substrate 2 of, for example, glass, an anode 3, a vacuum deposited organic hole injecting and hole transporting layer 4 comprised of a large polynuclear arylamine (I), a vacuum deposited electron injecting and electron transporting layer 5, and in contact therewith a low work function metal as a cathode 6. In the EL device, a luminescent zone, in which the electron-hole recombination takes place with subsequent light emission, encompasses the hole injecting/transporting layer and/or the electron injecting/transporting layer. Optionally, a fluorescent material, which is capable of emitting light subsequent to electron-hole recombination, may be added to the luminescent zone where the charge injecting/transporting component is utilized as a host material.

FIG. 2 illustrates another device configuration of the present invention comprising a single vacuum deposited luminescent layer 7, sandwiched between a cathode 6 and an anode 3. In embodiments of the present invention, the luminescent layer 7 is comprised of a hole injecting/transporting component comprised of a large polynuclear arylamine (I), an electron injecting/transporting component, and a light emitting component.

Illustrative examples of supporting substrates include polymeric components, glass and the like, and polyesters like MYLAR®, polycarbonates, polyacrylates, polymethacrylates, polysulfones, quartz, and the like. Other substrates can be selected provided they are essentially nonfunctional and can support the other layers. The thickness of the substrate can be, for example, from about 25 to over about 1,000 microns, depending, for example, on the structural demands of the device.

An anode contiguous to the substrate, includes positive charge injecting electrodes such as indium tin oxide, tin oxide, gold, or other materials including electrically conductive a-conjugated polymers such as polyaniline, polypyrrole, and the like with, for example, a work function equal to, or greater than about 4 electron volts. The thickness of the anode can range from about 10 to 5,000 Å with the preferred range being dictated by the optical constants of the anode material.

The hole injecting/transporting layer, such as layer 4, comprises a thin film of the large polynuclear arylamine as illustrated by formula (I)

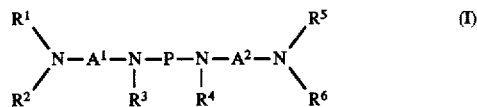

wherein $R^1$, $R^2$, $R^3$, $R^4$, $R^5$ and $R^6$ are aryl groups, $A^1$ and $A^2$ are biaryl groups, and P is a hydrocarbon bridge. Examples of arylamines (i) that are selected for the EL devices of the present invention include compounds (1) through (15)

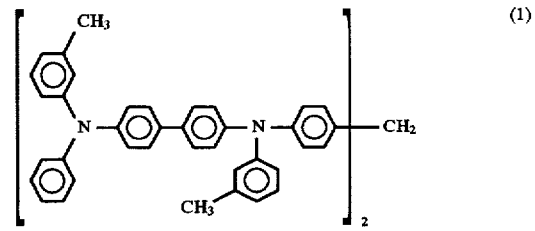

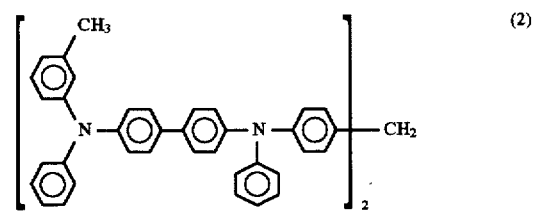

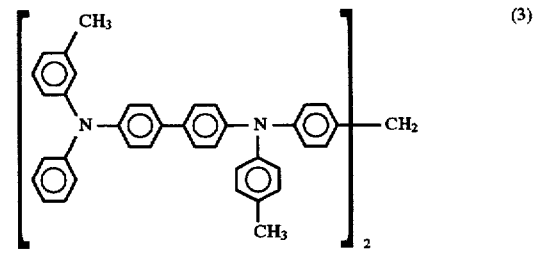

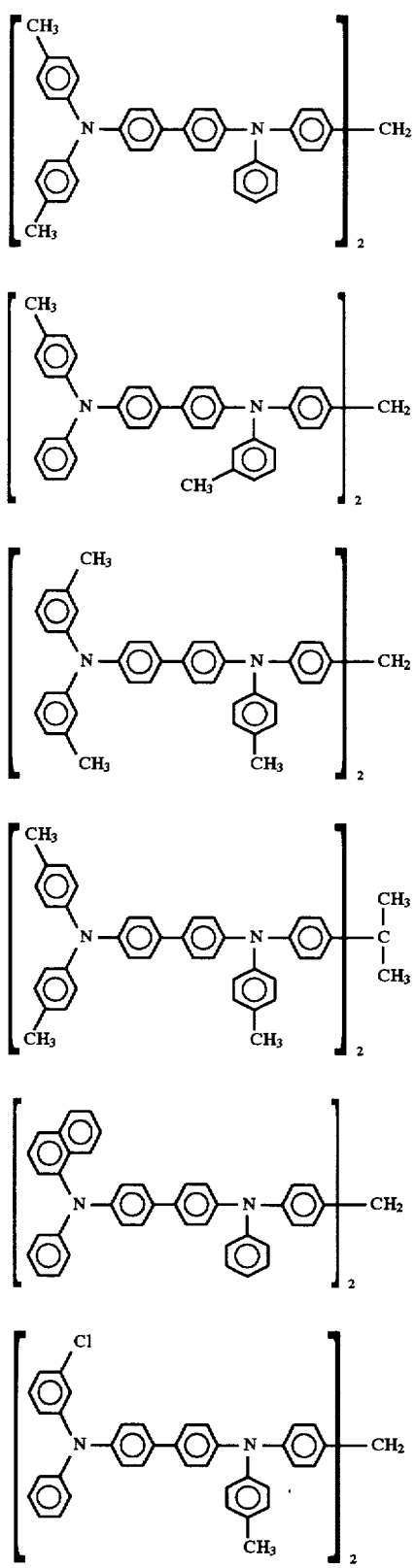
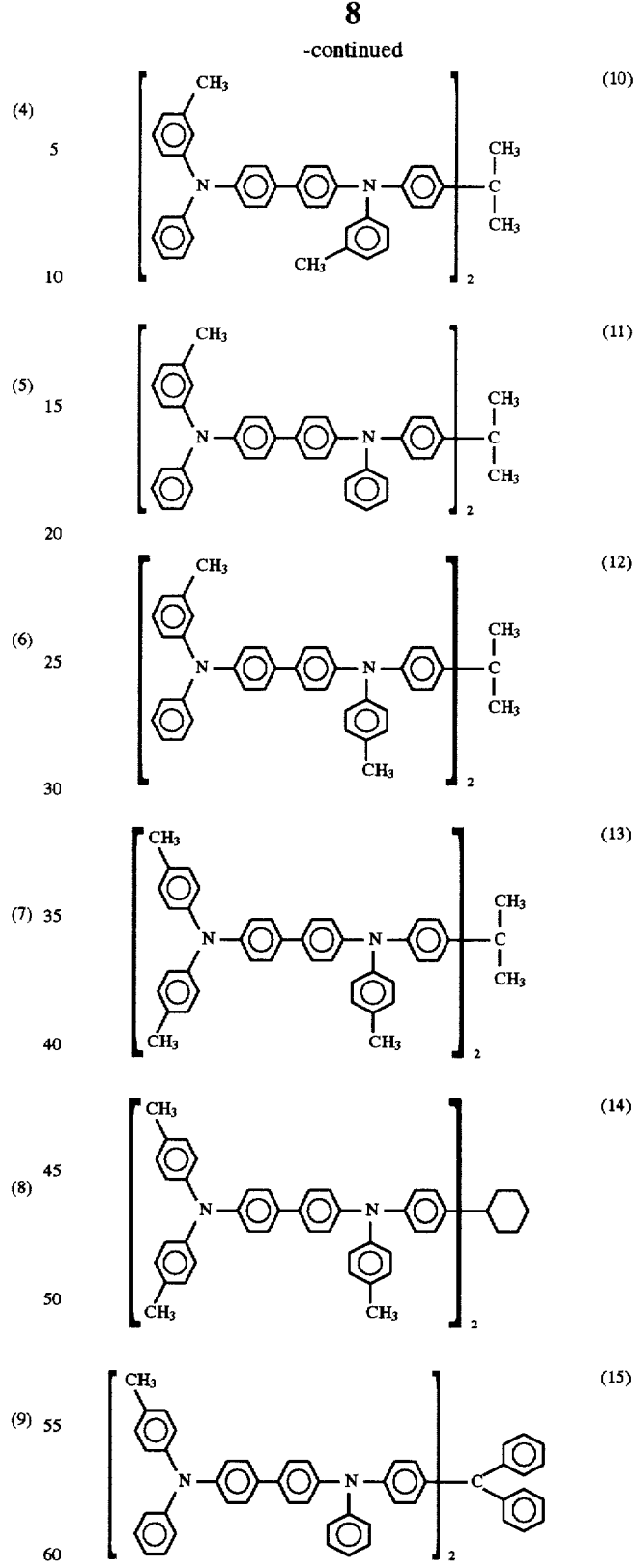
The polynuclear arylamines (I) of the present invention can be readily synthesized by the preparative process illustrated in Scheme 1.

SCHEME 1
Synthesis of Polynuclear Arylamine Derivative

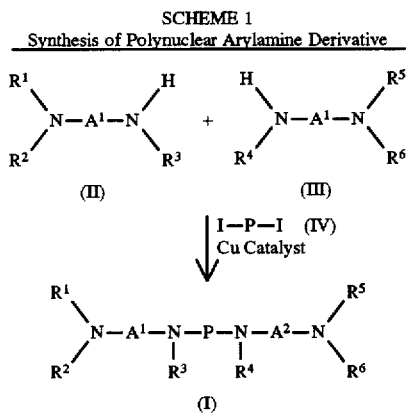

wherein $R^1$, $R^2$, $R^3$, $R^4$, $R^5$, and $R^6$ are as illustrated herein, such as aryl groups such as phenyl, tolyl, xylyl, chlorophenyl, naphthyl, and the like; P is a hydrocarbon bridge as illustrated herein, such as methylene, dimethylmethylene, 1,1-cyclohexylene, ethylene, polymethylene, arylene group, such as diphenylmethylene, phenylene, tolylene, xylylene, and chlorophenylene; and $A^1$ and $A^2$ are biaryl groups such as biphenyl, bitolyl, and the like.

As indicated in Scheme 1, the large polynuclear arylamines (I) are prepared by an Ullmann condensation of the arylamine intermediate (II) and/or (III) with the diiodide intermediate (IV). The condensation is generally accomplished in an inert solvent, such as dodecane, tridecane, toluene, xylene, petroleum ethers, and the like, at a temperature ranging from below 100° C. to over 280° C., and preferably from about 110° C. to about 250° C. Any type of copper catalysts suitable for Ullmann condensations, including copper powder, cuprous oxide, cuprous chloride, cuprous bromide, cuprous iodide, cupric sulfate, and the like, may be employed for the process of the present invention. Suitable molar ratios of the copper catalyst to arylamine intermediate (II) range from about 0.005 to about 1. The condensation can be accelerated with the addition, in an effective amount, of a base such as an alkaline metal hydroxide, or carbonate including potassium hydroxide, potassium carbonate, sodium hydroxide, and the like. The reaction mixture is then cooled to about room temperature, about 25° C., the product is isolated by known means, for example by filtration and chromatography, and identified by analytical methods, such as IR, NMR, carbon, hydrogen, nitrogen analysis.

The electron transport layer 5 is comprised of electron transport materials, such as those disclosed by U.S. Pat. No. 3,769,292, see for example column 6, line 54, to column 9, line 15. Examples of suitable electron transport materials include diarylbutadienes, stilbenes, optical brighteners, and metal chelated oxinoid compounds including chelates of oxine. One preferred electron transport material is tris(8-hydroxyquinolinate) aluminum, AlQ3, which may also function as an emitter in the EL devices.

The light emitting fluorescent material is present in an amount, for example, of from about 0.01 to about 10 weight percent, and preferably from about 0.5 to about 5 weight percent of the host transport layer. Examples of emitters or fluorescent dyes are illustrated by Tang et al. and include known compounds selected for this purpose, such as coumarin dyes, such as 7-diethylamino-4-methyl coumarin, 4,6-dimethyl-7-ethylamino coumarin, 4-methylumbelliferone, and the like, fluorescent 4-dicyanomethylene-4H-pyrans, such as 4-(dicyanomethylene)2-methyl-6-(p-dimethylaminostyryl)-4H-pyran, and the like, polymethine dyes, such as cyanines, merocyanines, complex cyanines and merocyanines, oxonals, hexioxonols, styryls, merostyryls, streptocyanines, and the like. Aromatic compounds, such as perylene, rubrene, and anthracene, can also be selected as emitter materials.

The cathode 6 is conveniently formed by deposition on the upper layer of the electron injecting/transporting layer 5. Cathode 6 is preferably comprised of magnesium, calcium, or aluminum. The cathode 6 is of a thickness of, for example, from about 10 to about 5,000 Å. The cathode 6 can be constructed of any metal including any low work function metal useful for this purpose. The cathode can also be formed from a combination of a low work function metal and at least one other metal. A low work function metal is a metal having a work function of, for example, equal to about, or less than about 4 eV. The lower the work function of the metal, the lower the voltage required for electron injection into layer 5 or 7.

Suitable low work function metals include metals of Group IIA or alkaline earth metals, Group III metals including rare earth metals and the actinide groups and metals. Alkaline earth metals are preferred because of their ready availability, low cost, ease of handling and minimal adverse environmental impact. Magnesium and calcium are particularly preferred. Low work function metals exhibiting work functions in the range of 3.0 to 4.0 eV are usually more stable than metals exhibiting lower work functions and are, therefore, preferred.

The cathode 6 may include a second metal for the purpose of increasing stability both during storage and operation. The second metal can be chosen from any metal other than alkaline metal. The second metal itself can be a low work function metal. Suitable examples of the second metal include the examples of metals for the first metal having a work function of less than about 4 eV.

As an alternative, the second metal can be selected from various metals having a work function greater than about 4 eV. This group includes elements more resistant to oxidation, and therefore, more commonly fabricated as metallic elements. The second metal contributes to the stability of cathode 6.

Suitable metals having a work function of 4 eV or greater include aluminum, the Group IB metals, metals in Groups IV, V, VI, and the Group VIII transition metals, particularly noble metals. Aluminum, copper, silver, gold, tin, lead, bismuth, tellurium and antimony are particularly preferred high work function second metals for incorporation into cathode 6.

A primary function of the second metal is to stabilize the first, low work function metal. A second function is to reduce sheet resistance of the cathode 6 as a function of the thickness of the cathode. This results in a highly stable, thin, transparent cathode 6 of acceptably low resistance level and high electron injection efficiency. A third function of the second metal is to facilitate vacuum vapor deposition of the first metal.

Suitable proportions of second metal are selected in the range of from about 1 percent to about 99 percent of the total metal component of cathode 6. Additional suitable cathode constructions, and suitable metals for the cathodes and functions of the metals are described by Tang et al.

Both anode 3 and cathode 6 of the organic EL device can be of any convenient form. A thin conductive layer can be coated onto a light transmissive substrate, for example, a transparent or substantially transparent glass plate or plastic film. The EL device can include a light transmissive anode 3 formed of tin oxide or indium tin oxide coated on a glass plate. Also, very thin light-transparent metallic anodes can be used, such as gold, and the like In addition, transparent or semitransparent thin layers of π-conjugated polymers, such as polyaniline, or polypyrrole, and the like, can be selected as anodes. Any light transmissive polymeric film can be employed as the substrate. Further, suitable forms of the anode 3 and cathode 6 are illustrated by Tang et al.

Additionally, in embodiments, the present invention is directed to organic layered EL devices comprised of a supporting substrate as illustrated herein, such as glass, a semitransparent layer of, for example, indium or tin oxide, an active single layer comprised of a polynuclear arylamine as illustrated herein, an emitter compound, an electron transport compound, and a low work function electrode as the top layer.

The disclosures of each of the patents recited herein are totally incorporated herein by reference.

The following Examples are provided to further define various species of the present invention, it being noted that these Examples are intended to illustrate and not limit the scope of the present invention.

EXAMPLE I

Synthesis of Compound (1)

Bis(4-iodophenyl)methane: In a 500 milliliter three-necked flask fitted with a water-cooled condenser, a mechanical stirrer, and a thermometer, was placed a mixture of acetic acid (200 milliliters), diphenylmethane (25.2 grams, 0.15 mol), iodine (34.2 grams, 0.135 mol), periodic acid (10.26 grams, 0.045 mol), concentrated sulfuric acid (10.0 milliliters), and water (60 milliliters). The contents in the flask were heated to 90° C., and stirred for 12 hours. The reaction was quenched by pouring the reaction mixture into 800 milliliters of ice water with vigorous stirring. The precipitate was collected by filtration, washed with water, and dried in a vacuum oven. The solid product resulting was further purified by recrystallization from hexane. Yield was 26.8 grams.

$^1$H-NMR (CDCl$_3$): δ 3.85 (s, 2H, methylene protons), 6.90 (d, J=8.4 Hz, 4H, aromatic protons), 7.60 (d, J=8.4 Hz, 4H, aromatic protons).

Compound (1): In a 100 milliliter round-bottomed flask was placed the above prepared bis(4-iodophenyl)methane (4.20 grams, 0.01 mol), N,N'-di-m-tolyl-N-phenylbenzidine (10.57 grams, 0.024 mol), copper (I) oxide (1.43 grams, 0.01 mmol), potassium hydroxide (8.06 grams, 0.145 mol) and ISOPAR M™ (8.0 milliliters). The flask was heated to 180° C. and stirred vigorously for 18.0 hours. The mixture was cooled to 120° C., and toluene (100 milliliters) was added. After stirring for 20 minutes, the toluene layer was separated, and then mixed with alumina at reflux for 1.0 hour. The alumina was filtered off and the filtrate was evaporated and chromatographed on silica gel with hexane-toluene (5:2) as eluent to provide a crude product which was further purified by recrystallization from a mixed solvent of hexane and ethyl acetate. Yield was 7.5 grams.

$^1$H-NMR (CDCl$_3$): δ 2.26 (s, 12H, methyl protons), 3.90 (s, 2H, methylene protons), 6.81 to 7.28 (m, 42H, aromatic protons), 7.41 to 7.46 (m, 8H, aromatic protons).

Compound 1 corresponds to the arylamine of Formula (1).

EXAMPLE II

Synthesis of Compound (2)

The titled compound was synthesized in accordance with the procedure of Compound (1) as described in Example I except that N,N'-diphenyl-N-m-tolylbenzidine was utilized in place of N,N'-di-m-tolyl-N-phenylbenzidine. Yield was 78 percent.

$^1$H-NMR (CDCl$_3$): δ 2.25 (s, 6H, methyl protons), 3.91 (s, 2H, methylene protons), 6.80 to 7.28 (m, 44H, aromatic protons), 7.40 to 7.45 (m, 8H, aromatic protons).

EXAMPLE III

Synthesis of Compound (10)

2,2-Bis(4-iodophenyl)propane: In a 500 milliliter two-necked flask equipped with an addition funnel and a water-cooled condenser was placed 2,2-diphenylpropane (10.0 grams, 0.051 mmol), acetic acid (100 milliliters), iodine (12.9 grams, 0.051 mmol), and concentrated sulfuric acid (23.76 grams). In the addition funnel was placed nitric acid (6.8 milliliters). The mixture in the flask was heated to 60° C., and the nitric acid was added dropwise over a period of 20 minutes. After completion of the addition, the reaction mixture was heated to 80° C. and stirred at this temperature for an additional 20 minutes. The reaction was quenched by pouring the reaction mixture into an ice water (500 milliliters). The precipitated solid was collected by filtration, washed with water, methanol and dried in vacuum. The pale yellow solid was further purified by recrystallization from hexane to afford colorless crystals. Yield was 16.3 grams, and m.p. 114° to 115° C.

$^1$H-NMR (CDCl$_3$): δ 1.61 (s, 6H, methyl protons), 6.90 (d, J=8.4 Hz, 4H, aromatic protons), 7.60 (d, J=8.4 Hz, 4H, aromatic protons).

Compound (10): In a 100 milliliter round-bottomed flask was placed 2,2-bis(4-iodophenyl)propane (4.48 grams, 0.01 mol), N,N'-di-m-tolyl-N-phenylbenzidine (10.03 grams, 0.022 mol), cupric sulfate pentahydrate (0.163 gram, 0.66 mmol), potassium carbonate (2.76 grams, 0.02 mol), and n-tridecane (7.0 milliliters). The mixture in the flask was heated to 230° C. and stirred vigorously for 18.0 hours. The mixture was cooled to 120° C., and toluene (100 milliliters) was added. After stirring for 20 minutes, the toluene layer was separated, and then mixed with alumina at reflux for 1.0 hour. The alumina was filtered off, and the filtrate was evaporated and chromatographed on silica gel with hexane-toluene (5:2) as eluent to give a crude product which was further purified by recrystallization from a mixed solvent of hexane and ethyl acetate. Yield was 5.5 grams.

$^1$H NMR (CDCl$_3$): δ 1.68 (s, 6H, methyl protons), 2.25 (s, 12 H, methyl protons), 6.82–7.29 (m, 42H, aromatic protons), 7.43 (d, J=8.7 Hz, 8H, aromatic protons).

EXAMPLE IV

Synthesis of Compound (11)

The titled compound was synthesized in accordance with the procedure for Compound (1) as described in Example III except that N,N'-diphenyl-N-m-tolylbenzidine was utilized in place of N,N'-di-m-tolyl-N-phenylbenzidine. Yield was 69 percent.

$^1$H-NMR (CDCl$_3$): δ 1.69 (s, 6H, methyl protons), 2.25 (s, 6 H, methyl protons), 6.81 to 7.29 (m, 42H, aromatic protons), 7.42 (d, J=8.5 Hz, 8H, aromatic protons).

EXAMPLE V

A 50 milliliter×50 milliliter indium-tin oxide coated glass plate (ITO glass) was etched with dilute HCl to form 6 millimeter strips, followed by washing with deionized water and drying in a vacuum oven at 60° C. for 1 hour. Immediately before use, the glass was treated with UV ozone for 0.5 hour. The ITO glass was then placed in a vacuum deposition chamber for deposition of the organic layers. The deposition rate and final thickness was controlled by an Inficon Model IC/5 controller. Under a pressure of less than $5 \times 10^{-6}$ torr, the hole transport compound (1) as obtained in Example I was first thermally evaporated from an electrically heated tantalum boat at a rate of 0.4 nanometer per second to deposit a 80 nanometer thick layer on the ITO glass. Subsequently, the electron injecting and electron transporting layer, which can also function as an emitter, compound, tri(8-hydroxyquinolinate) aluminum, purchased from Aldrich Chemicals, was evaporated in the same manner to form a 80 nanometer layer on top of the hole transport layer. Finally, ten 1 millimeter wide cathodes of Mg:Ag alloy were formed through a patterned mask on top of the above organic layers by thermal evaporation from two independently controlled tantalum boats containing Mg and Ag, respectively. The typical composition was 5:1 in atomic ratio of Mg to Ag. A 100 nanometers layer of the alloy was formed at a total deposition rate of 0.5 nanometer per second. Finally, about 200 nanometers of Ag were overcoated on the Mg:Ag cathode for the purpose of protecting the reactive Mg from ambient moisture.

The device as prepared above was retained in a dry box which was continuously purged with nitrogen gas. Its performance was assessed by measuring its current-voltage characteristics and light output under a direct current measurement. The current-voltage characteristics were determined with a Keithley Model 238 High Current Source Measure Unit. The ITO electrode was always connected to the positive terminal of the current source. At the same time, the light output from the device was monitored by a silicon photodiode.

The present device emitted green light and provided a luminance of 5,500 cd/m$^2$ at a dc voltage of 20 volts. The operational stability of the device was evaluated at 20° C. under a stress condition of a high constant current density of 67 mA/cm$^2$. The initial light intensity was 1,200 cd/m$^2$, an intensity level that is well in excess of that required for practical application. The light intensity decreased slowly overtime, and a 70 percent reduction in light intensity was observed after 110 hours of continuous operation. In addition, the device displayed no changes in the current-light intensity characteristics even after it was subjected to a temperature of 40° C. for 72 hours.

COMPARATIVE EXAMPLE

A comparative EL device was fabricated in accordance with the procedure of Example V except that a known prior art hole transport compound, N,N'-diphenyl-N,N'-bis(3-methylphenyl)1,1'-biphenyl-4,4'-diamine was utilized in place of N,N-bis-[4'-(N-phenyl-N-m-tolylamino)-4-biphenylyl]-aniline (1).

This comparative device provided a luminance of 4,700 cd/m$^2$ at a DC voltage of 20 volts. Under a constant current density of 67 mA/cm$^2$, the present device afforded an initial light intensity of 910 cd/m$^2$, but the light intensity decreased rapidly, registering a 70 percent reduction after only 45 hours of continuous operation. Furthermore, the device was rendered nonfunctional after it had been subjected to a temperature of 40° C. for 72 hours.

EXAMPLE VI

An EL device was fabricated in accordance with the procedure of Example V except that the hole transport compound (2) as prepared in Example II was utilized in place of hole transport compound (1).

The device emitted green light and provided a luminance of 4,875 cd/M$^2$ at a dc voltage of 20 volts. Under a constant current density of 67 mA/cm$^2$, the present device afforded an initial light intensity of 950 cd/m$^2$, and the light intensity registered a 70 percent reduction after 105 hours of continuous operation. In addition, the device displayed no changes in the current-light intensity characteristics after it was subjected to a temperature of 40° C. for 72 hours.

EXAMPLE VII

An EL device was fabricated in accordance with the procedure of Example V except that hole transport compound (10) as prepared in Example III was utilized in place of hole transport compound (1).

The device emitted green light and provided a luminance of 4,850 cd/M$^2$ at a dc voltage of 20 volts. Under a constant current density of 67 mA/cm$^2$, the present device afforded an initial light intensity of 1,010 cd/m$^2$, and the light intensity registered a 70 percent reduction after 85 hours of continuous operation. In addition, the device displayed no changes in the current-light intensity characteristics after it was subjected to a temperature of 40° C. for 72 hours.

EXAMPLE VIII

An EL device was fabricated in accordance with the procedure of Example V except that hole transport compound (11) prepared in Example IV was utilized in place of hole transport compound (1).

The device emitted green light and provided a luminance of 4,750 cd/M$^2$ at a dc voltage of 20 volts. Under a constant current density of 67 mA/cm$^2$, the present device afforded an initial light intensity of 850 cd/m$^2$, and the light intensity registered a 70 percent reduction after 97 hours of continuous operation. In addition, the device displayed no changes in the current-light intensity characteristics after it was subjected to a temperature of 40° C. for 72 hours.

Other embodiments and modifications of the present invention may occur to those of ordinary skill in the art subsequent to a review of the present application and the information presented herein; these embodiments and modifications, as well as equivalents thereof, are also included within the scope of this invention.

What is claimed is:

1. An electroluminescent device comprising in sequence a supporting substrate, an anode, a hole injecting component and a cathode, wherein the hole injecting component is a polynuclear arylamine as represented by the following formulae (7), (10), (11), (12), (13) and (15):

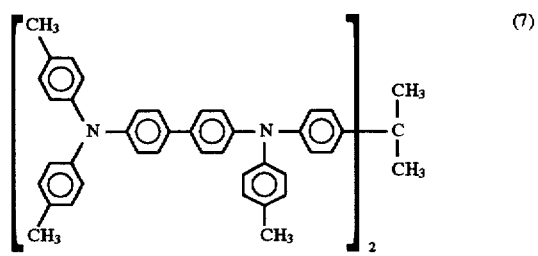
(7)

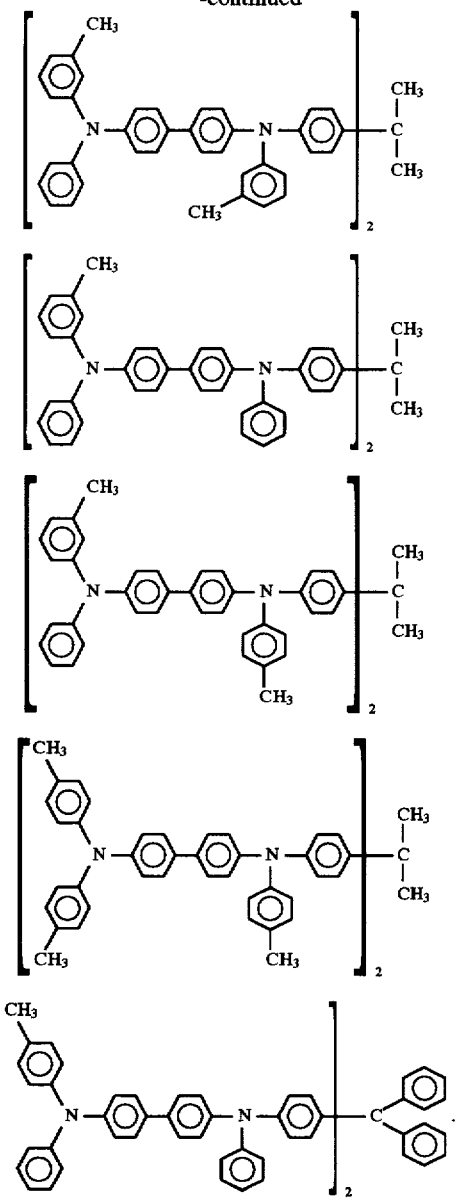

2. The electroluminescent device of claim 1 wherein there is further included an electron injecting component selected from the group consisting of diarylbutadiene, stilbene, or 2,5-diaryl-1,3,4-oxadiazole.

3. The electroluminescent device of claim 2 wherein the electron injecting component further functions as an electron transporting component.

4. A device in accordance with claim 2 wherein said arylamine functions as a hole injecting component and as a hole transporting component, and said electron injecting component further functions as an electron transporting component.

5. The electroluminescent device of claim 1 further comprising an electron injecting component which is a metal complex of 8-hydroxyquinoline.

6. The electroluminescent device of claim 5 wherein the electron injecting component further functions as an electron transporting component.

7. The electroluminescent device of claim 1 wherein the substrate is a polymer, a metal, a semiconductor or glass.

8. The electroluminescent device of claim 1 wherein the anode is indium tin oxide.

9. The electroluminescent device of claim 1 wherein the anode is comprised of indium tin oxide.

10. The electroluminescent device of claim 1 wherein the anode is a high work function metal of gold or platinum.

11. The electroluminescent device of claim 1 wherein the anode is the conductive polymer polyaniline.

12. The electroluminescent device of claim 1 wherein the supporting substrate is glass, the anode is an indium tin oxide, the cathode is a magnesium silver alloy, and the device further comprises an electron injecting component which is an 8-quinolinato aluminum complex.

13. The electroluminescent device of claim 1 wherein the supporting substrate is of a thickness of from about 25 to about 1,000 microns, the anode is of a thickness of from about 10 to about 500 nanometers, and the cathode is of a thickness of from about 5 nanometers to about 5 micrometers.

14. An electroluminescent device comprising in sequence a supporting substrate, an anode, a hole injecting component and a cathode, wherein the hole injecting component is a polynuclear arylamine as represented by the following formulae (8) and (9)

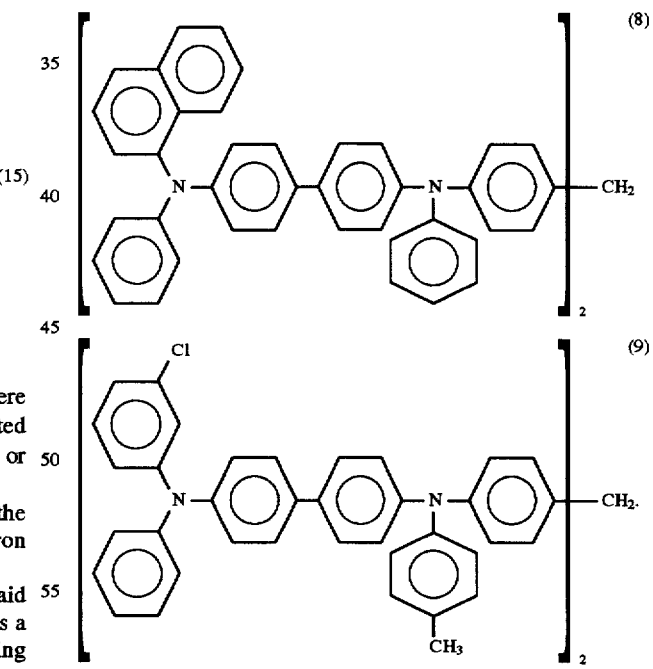

* * * * *